(12) United States Patent
Hundstad et al.

(10) Patent No.: US 9,964,399 B2
(45) Date of Patent: May 8, 2018

(54) NON-DESTRUCTIVE MAPPING OF SURFACE CONDITION TO EVALUATE WEAR CONDITIONS

(71) Applicants: BWXT Nuclear Energy, Inc., Charlotte, NC (US); BWXT Canada Ltd., Cambridge (CA)

(72) Inventors: Richard W. Hundstad, Lynchburg, VA (US); Rajendra Persad, Lynchburg, VA (US); Nathaniel R. Bruns, Breslau (CA); Daniel E. Gammage, Ancaster (CA)

(73) Assignees: BWXT Nuclear Energy, Inc., Charlotte, NC (US); BWXT Canada Ltd., Cambridge (CA)

(*) Notice: Subject to any disclaimer, the term of this patent is extended or adjusted under 35 U.S.C. 154(b) by 51 days.

(21) Appl. No.: 14/207,140

(22) Filed: Mar. 12, 2014

(65) Prior Publication Data

US 2014/0268176 A1    Sep. 18, 2014

Related U.S. Application Data

(60) Provisional application No. 61/794,990, filed on Mar. 15, 2013.

(51) Int. Cl.
| | |
|---|---|
| *G01B 11/00* | (2006.01) |
| *G01N 21/00* | (2006.01) |
| *G01B 11/02* | (2006.01) |
| *G01N 21/88* | (2006.01) |
| *G01B 11/25* | (2006.01) |
| *F22B 37/00* | (2006.01) |

(52) U.S. Cl.
CPC .......... *G01B 11/026* (2013.01); *F22B 37/003* (2013.01); *G01B 11/2518* (2013.01); *G01N 21/8806* (2013.01); *G01N 21/8851* (2013.01)

(58) Field of Classification Search
CPC ................... G01N 21/8806; G01N 21/8851
See application file for complete search history.

(56) References Cited

U.S. PATENT DOCUMENTS

| | | |
|---|---|---|
| 6,174,392 B1 | 1/2001 | Reis |
| 6,952,095 B1 | 10/2005 | Goldfine et al. |
| 7,253,908 B2 | 8/2007 | Vaccaro et al. |

(Continued)

OTHER PUBLICATIONS

ScanControl: Compact 2D/3D profile sensor with integrated controller, Micro-Epsilon, pp. 1-8, Sep. 2012.*

(Continued)

*Primary Examiner* — Hina F Ayub
*Assistant Examiner* — Amanda Merlino
(74) *Attorney, Agent, or Firm* — Nelson Mullins Riley & Scarborough LLP

(57) ABSTRACT

A component, such as a cyclonic steam separator baseplate of a steam generator, includes a surface subject to degradation during operation of the system in which the component is disposed. A profile is acquired of the surface of the component using an optical surface profilometry system concurrent with an image of the surface. A condition, such as degradation of the component is classified based on the acquired profile and image of the surface of the component. Component conditions may be monitored over time, trended, and classified as requiring maintenance, repair, or replacement.

17 Claims, 3 Drawing Sheets

(56) References Cited

U.S. PATENT DOCUMENTS

| | | |
|---|---|---|
| 7,508,504 B2 | 3/2009 | Jin et al. |
| 7,630,086 B2 | 12/2009 | Oak et al. |
| 7,842,113 B2 | 11/2010 | Albrecht et al. |
| 2012/0019809 A1 | 1/2012 | Shirley et al. |

OTHER PUBLICATIONS

Scan Control: Compact 2D/3D profile sensor with integrated controller, Micro-Epsilon, pp. 1-8, Sep. 2012, http://www.ien.eu/uploads/tx_etim/26789_MicroEpsilon_JanFeb09.pdf.*

International Search Report and Written Opinion for PCT/2014/024741 dated Jul. 29, 2014.

* cited by examiner

NON-DESTRUCTIVE MAPPING OF SURFACE CONDITION TO EVALUATE WEAR CONDITIONS

This application claims the benefit of U.S. Provisional Application No. 61/794,990 filed Mar. 15, 2013 and titled "Non-Destructive Mapping of Surface Condition to Evaluate Wear Conditions" and is hereby incorporated by reference in its entirety herein.

BACKGROUND

The following relates to the non-destructive examination arts, component maintenance arts, and related arts.

Heat exchangers, such as steam generators, are commonly used in electric power generation. A typical arrangement of a power plant includes a nuclear, fossil fuel-fired boiler, or other water boiler system that heats water to a boiling, sub-cooled, or other heated state. The output is a mixed-phase, two-component water/steam mixture that is fed into a steam separator where dry steam is separated from the mixture and used to drive a turbine or to perform other useful work. In a variant approach, a steam generator receives a saturated liquid and also receives secondary coolant in the form of liquid water, and heat transfer in the steam generator results in the boiling of the secondary coolant to produce the steam while maintaining fluid isolation between the saturated liquid (that is, primary flow) and the secondary coolant. This latter arrangement is beneficial in systems such as pressurized water (nuclear) reactors (PWR) in which the reactor may impart radioactivity on the primary coolant.

In such steam generators, the quality of the steam is an important consideration. High quality steam is desirable as it contains little or (ideally) no liquid water. Liquid water in steam can lead to moisture-induced degradation of components, including, for example, turbine components, that are exposed to such steam.

Various technologies can be employed to perform steam separation, including centrifugal separators, scrubbers and chevrons. Alternatively, steam separation can be negated via the use of once-through steam generators. The secondary side fluid exits once-through steam generators in a superheated state, thus removing the need for steam separation.

In cyclone or centrifugal steam separator components, high-speed rotation is imparted into the fluid flow so as to separate steam and water by centrifugal force. Cyclonic separators are well-suited for use as a second stage or drying phase in the steam generator, where high flow rates of (mostly) steam facilitate efficient centrifugal separation. Cyclonic steam/water separators (also called moisture separators, steam separators, or similar nomenclature) can be active devices, for example, using a rotating turbine to impart rotational flow, or can be passive components in which fixed vanes are oriented to impart rotation to an existing high-velocity steam flow. Surfaces of the cyclonic separator are configured to collect moisture from the rotational flow while allowing the dried steam to pass. Passive secondary cyclonic steam separators are commonly used to improve steam quality in steam generators.

Because cyclonic steam separators are exposed to moisture during normal operation, the potential exists for moisture-induced surface degradation. The cyclonic steam separator components may be visually inspected during steam generator maintenance outages, sometimes including photographic recordation of surface condition. The inspection can be hampered by time constraints and is also usually coordinated with other concurrent maintenance operations introducing further timing and scheduling constraints.

Disclosed herein are improvements that provide various benefits that will become apparent to the skilled artisan upon reading the following.

BRIEF SUMMARY

In one representative embodiment of the disclosure, a method comprises acquiring a profile of a surface of a component by an optical surface profilometry system, and classifying a condition of the surface based on the acquired profile.

In another representative embodiment of the disclosure, a non-transitory storage medium stores instructions readable and executable by an electronic data processing device to perform operations, which include controlling an optical surface profilometry system to acquire a surface profile of a plurality of components and classifying the plurality of components based on the acquired surface profiles respective to degradation of the plurality of components.

In a further representative embodiment of the disclosure, an inspection system comprises an optical surface profilometry system configured to acquire a profile of a surface of a component, a non-transitory storage medium storing instructions readable and executable by an electronic data processing device, and an electronic data processing device configured to read and execute instructions stored on the non-transitory storage medium to control the optical surface profilometry system to acquire the profile and to classify a condition of the surface based on the acquired profile.

In yet another representative embodiment of the disclosure, a method of inspecting a component subject to degradation comprises acquiring at a first time a first profile of a surface of the component with an optical surface profilometry system and a first image of the surface of the component and acquiring at a second time a second profile of the surface of the component with the optical surface profilometry system and a second image of the surface of the component.

BRIEF DESCRIPTION OF THE DRAWINGS

The invention may take form in various components and arrangements of components, and in various process operations and arrangements of process operations. The drawings are only for purposes of illustrating preferred embodiments and are not to be construed as limiting the invention.

DETAILED DESCRIPTION OF THE PREFERRED EMBODIMENTS

Figure 1:
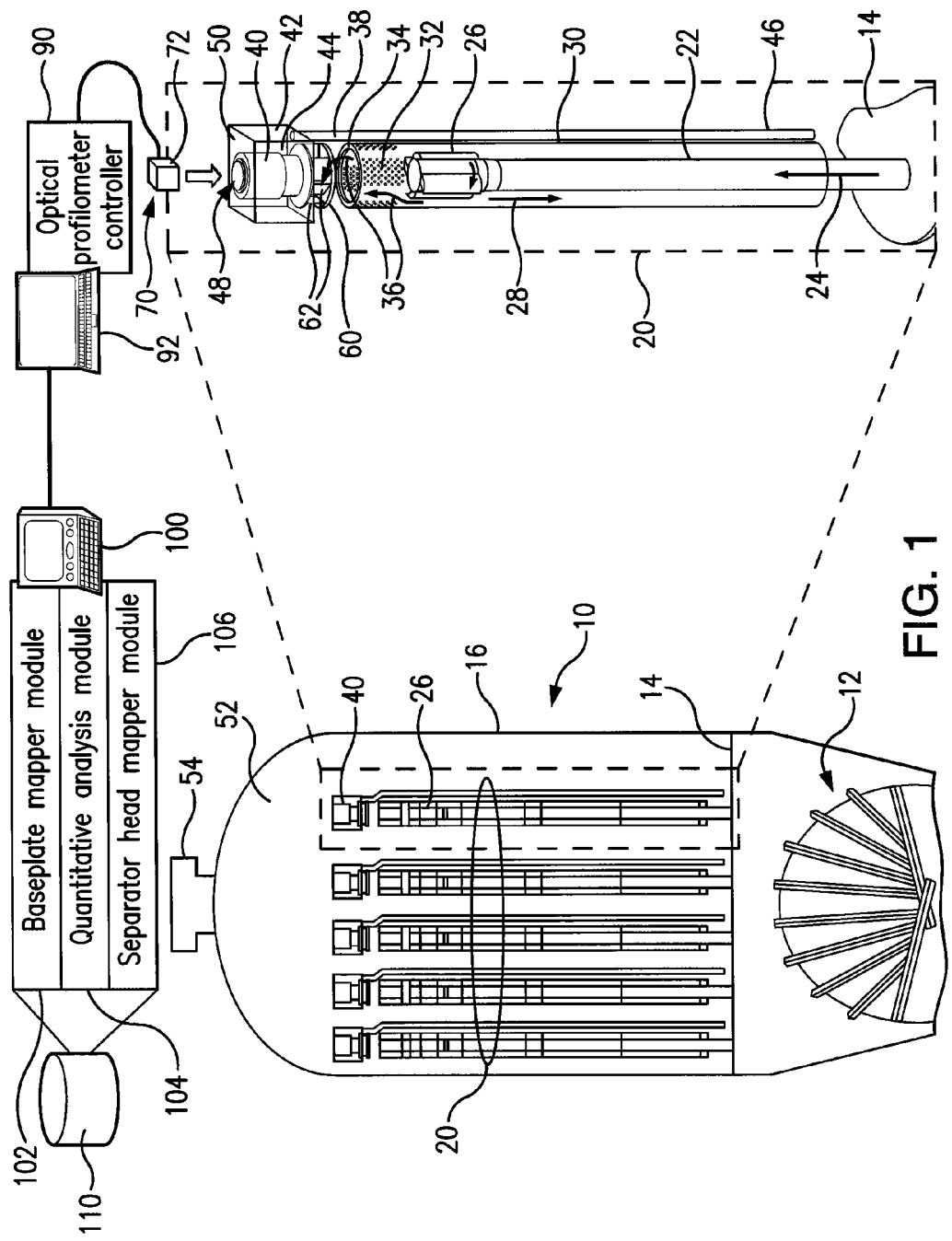
FIG. 1 diagrammatically shows a steam generator with cyclonic steam separators and an inspection system for the cyclonic steam separators employing inspection by optical surface profilometry.

It is recognized herein that visual inspection of component surfaces, such as for example, cyclonic steam separator surfaces, has substantial difficulties. It is qualitative in nature, making it difficult to establish standards for deciding when to repair or replace a component. Further, trending analysis and predictive modeling is not possible using visual inspection alone. Moreover, inspections may be performed on an infrequent basis, for example, during scheduled inspections generally coinciding with plant refueling, maintenance, or inspection outages, with many months between successive outages. Even if a photographic record of each visual inspection is generated, comparing photographs acquired many months apart is a subjective process making tracking of the surface degradation over time difficult and imprecise.

For example, visual inspection of a cyclonic steam generator baseplate that has been operated in the steam separator section of a steam generator may exhibit discoloration that is readily detected visually (including by photographic recordation). This may suggest that baseplate degradation is due to some type of chemical interaction, for example, oxidation. Surface degradation also entails removal etching, or pitting of material, and in extreme cases such degradation can lead to openings forming in the baseplate. Thus, component degradation is a complex process.

As disclosed herein, the use of optical surface profilometry, for example, laser profilometry in the illustrative examples, provides improved inspection of component surfaces. Optical surface profilometry techniques are typically sensitive to changes in surface profile, for example, due to mechanical, chemical, or mechanical-chemical etching. However, optical surface profilometry is typically not sensitive to chemical changes in a surface absent associated buildup or removal of material. Nonetheless, the inventors have found a strong correlation between visually observed surface degradation and surface mapping by optical surface profilometry. Moreover, optical surface profilometry provides substantial benefits over visual inspection.

Optical surface profilometry is quantitative, rather than qualitative as in visual inspection. Optical surface profile acquisition systems can be constructed to employ few user adjustments (or even no user adjustments at all), which facilitates repeatability and fair comparison between optical surface profiles acquired during component inspections that occur months or years apart. A further advantage of the disclosed optical surface profilometry inspection approach is that a three-dimensional (3D) surface profile can be readily compared with a photograph or digital image of the surface (the third dimension is the depth, so that the 3D surface profile can be represented as a two-dimensional (2D) map analogous to a photograph or digital image), so that the optical surface profilometry inspection is complementary with existing visual inspection techniques (including photographic or digital image recordation of the visual inspection). Indeed, in some embodiments the inspection apparatus includes both an optical surface profilometry instrument and an on-board or integrated imaging device, such as a camera, digital camera, image scanner, or 3D scanner (hereinafter referred to as a "camera"), such that photographs or digital images can be taken concurrently or in conjunction with the acquisition of the optical surface profilometry data to validate or ensure consistency of the data and to develop evaluation criteria for the condition of the component or the component surface.

Without being limited to any particular theory of operation, it is believed that surface degradation in an operating cyclonic steam separator is a corrosive process that produces physical surface cavitation, etching, or the like which is readily measured by surface profilometry. Visually perceived baseplate discoloration caused by chemical interaction is therefore likely to be associated with concomitant changes in the surface profile that are measurable by optical surface profilometry. Again, without being limited to any particular theory of operation, it is believed that the dominant surface degradation mechanism in operating cyclonic steam separators is flow accelerated corrosion due to fast-flowing water or wet steam. Flow accelerated degradation depends on factors such as water chemistry, flow rate and volume (higher flow leads to more aggressive flow-accelerated surface degradation), and the surface material.

With reference to FIG. 1, the disclosed inspection approach is described with reference to an illustrative steam generator 10, the upper portion of which is shown in diagrammatic representation in FIG. 1. The illustrative steam generator 10 includes a steam generation mechanism 12 performing the steam separation. The steam generation mechanism 12 may employ any steam generation technology as described previously herein. In the illustrative steam generator 10, the steam is generated from secondary coolant water heated by heated primary coolant flow output by a PWR or the like in a tube-and-shell structure shown in the steam generation mechanism 12. In other embodiments, the steam is generated directly from the heated water/steam mixture produced by a fossil fuel boiler, boiling water (nuclear) reactor (BWR), or the like.

The output of the steam generation mechanism 12 is "wet" steam of relatively low quality insofar as it contains substantial moisture content. This wet steam is at substantial positive pressure, and flows upward through passages or flow holes (not shown) in a separator deck 14 to enter a steam drum 16 containing a plurality of steam separator units 20. FIG. 1 illustrates five steam separator units 20 in the steam drum 16; however, more generally the number of steam separator units in the separator head is chosen based on the performance of the separator, the steam volume, and the quality of the steam entering the steam drum 16 through the separator deck 14, and the working steam quality requirements (these factors determine the amount of moisture that needs to be removed). The steam separators 20 are typically arranged in a two-dimensional array or other two-dimensional pattern over the area of the separator deck 14.

For illustrative purposes, a perspective view of one steam separator unit 20 is shown in the right-hand side of FIG. 1. The illustrative steam separator unit 20 includes a riser tube 22 connected at its lower end with an orifice in the separator deck to receive a pressure-driven upward flow of wet steam 24 from the steam generation mechanism 12 located below the separator deck 14. The riser tube 22 extends upward to deliver the upward flow of wet steam 24 into an illustrative curved-arm primary separator 26 or other primary separator device. The illustrative curved-arm primary separator 26 employs curved tubes to form a tortuous path that tends to cause moisture to condense out of the flow onto tube surfaces. The condensed moisture 28 flows down the surfaces of a return cylinder 30 arranged coaxially around the riser tube 22 to return to the lower portion of the steam generator 10 to be reprocessed by the steam generation mechanism 12, or alternatively may flow to a condensate reservoir (not shown). The upper end of the illustrative return cylinder 30 includes return cylinder perforations 32 and an upper retaining lip 34 that help capture condensate. The primary separator 26 outputs steam 36 of higher quality (as compared with the wet steam 24 entering the riser tube 22). The steam 36 passes through an interstage space 38 and into a cyclonic (or centrifugal) steam separator 40 contained in a second-stage compartment 42. The cyclonic steam separator 40 provides a second stage of steam separation which generates additional condensate 44 that flows down a drain tube 46 extending downward from the second-stage compartment 42 to join the condensate 28 from the first-stage steam separation, or is connected to collect the condensate 44 elsewhere. The cyclonic steam separator 40 has an upper orifice 48 through which "dried" steam flows out, which is of still higher quality (as compared with the steam 36 output by the primary separator 26). Optionally, an upper surface 50 of the second-stage compartment 42 includes bypass holes (not visible in FIG. 1) to enable steam 36 to bypass (or partially bypass) the cyclonic steam separator 40 in the event of a constriction or other failure in the cyclonic steam separator 40.

The high quality steam output through the orifices 48 of the cyclonic steam separators 40 of the steam separator units 20 pressurize an upper plenum 52 of the steam drum 16. The high quality pressurized steam in the upper plenum 52 is suitably output through an output flange 54 of the steam drum 16 and delivered via suitable steam piping (not shown) to a turbine or other device that employs the steam to perform useful work. It is to be appreciated that the steam drum 16 is shown diagrammatically, and omits various optional features such as access ports, pressure relief valves, and so forth. In some embodiments, the steam drum 16 has a lower flange (not shown) connecting the separator head to the lower portion of the steam generator, which may be removed to provide access to the internal components. Still more generally, the steam generator diagrammatically shown in FIG. 1 is merely an illustrative example of an operational environment employing cyclonic steam separators to dry steam. The skilled artisan understands that cyclonic steam separators find application in diverse types and designs of steam generators, as well as in other applications in which cyclonic steam separators can be usefully employed to improve steam quality.

Figure 2:
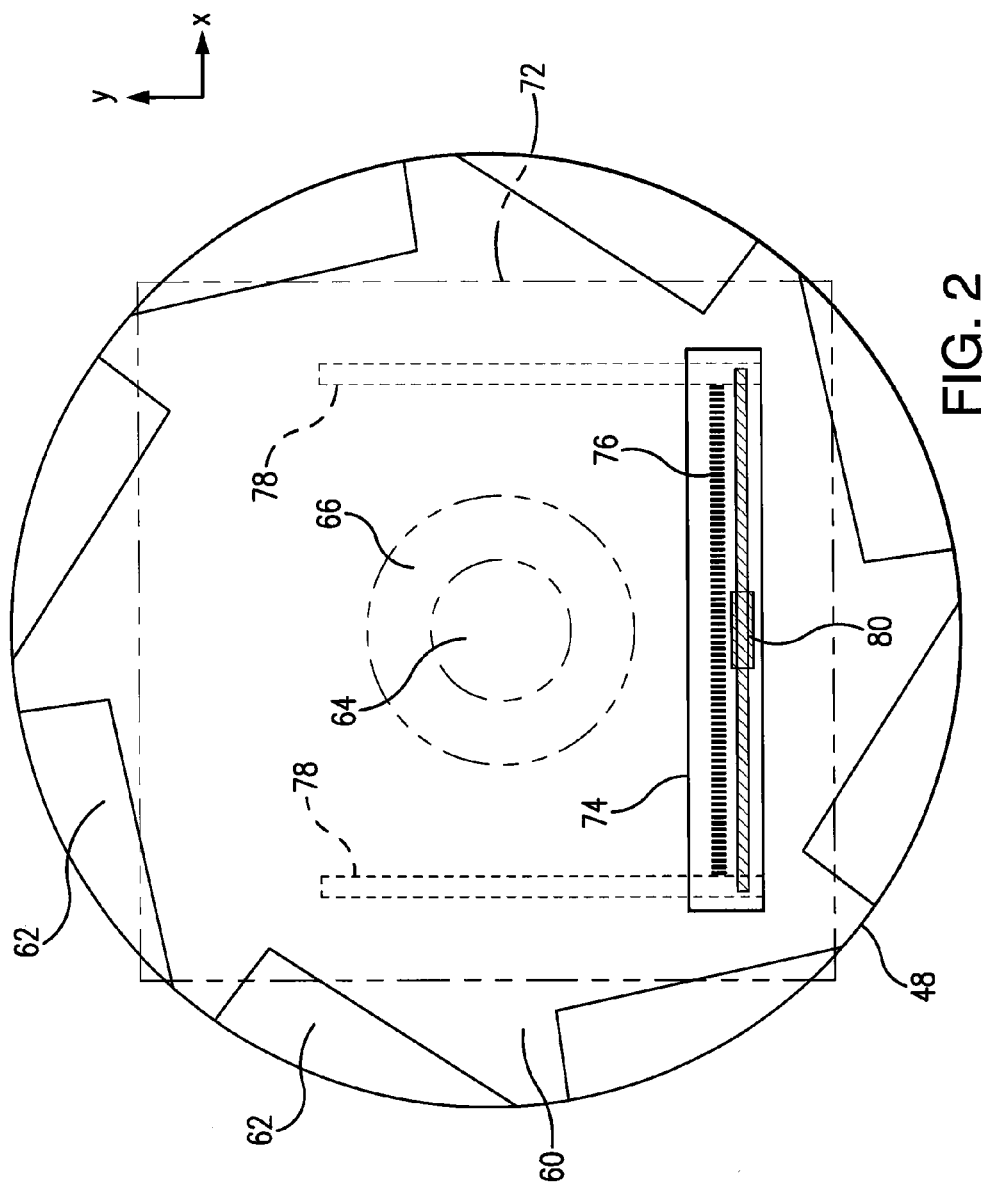
FIG. 2 diagrammatically shows an overhead view of a baseplate and vanes as seen through the orifice of one of the cyclonic steam separators of the steam generator of FIG. 1.

With continuing reference to FIG. 1 and with further reference to FIG. 2, the cyclonic steam separator 40 includes a baseplate 60 and a set of fixed vanes 62 located at outboard positions along the circumference of the baseplate 60. FIG. 2 diagrammatically shows an overhead view of the baseplate 60 and vanes 62 as seen through the orifice 48 of the cyclonic steam separator 40. During normal operation, the flow of steam 36 output by the primary separator 26 enters the gaps between the outboard vanes 62 and is urged into a rotating (i.e. cyclonic) flow pattern by the vanes 62. This rotating steam flow circulates over the surface of the baseplate 60, and moisture in the steam is removed by centrifugal force to condense onto the surface of the baseplate 60 and on other surfaces inside the cyclonic steam separator 40. As diagrammatically shown in FIG. 2, it has been found that the surface of the baseplate 60 over which the rotating steam flow is formed exhibits surface degradation over time, as evidenced by visually observed discoloration of the surface of the baseplate 60. Typically, the visually observed surface degradation is principally seen near the center of the baseplate 60, diagrammatically indicated in FIG. 2 as a central degradation region 64, and/or in an annular surface region around the center of the baseplate 60, diagrammatically indicated in FIG. 2 as an annular degradation region 66. Without being limited to any particular theory of operation, it is believed that the dominant surface degradation mechanism producing the surface degradation 64, 66 is flow accelerated corrosion due to the fast-flowing rotation of water or wet steam.

With continuing reference to FIGS. 1 and 2, the surface degradation regions 64, 66 are characterized by an optical surface profilometry device 70 which is suitably contained in a housing or enclosure 72 (as shown in FIG. 1 and indicated diagrammatically in phantom lines in FIG. 2) or mounted on an open frame or support (not shown). The optical surface profilometry device 70 is lowered onto or over the orifice 48 of the cyclonic steam separator 40 as indicated by a diagrammatic arrow in FIG. 1, and views the baseplate 60 and inboard edges of the outboard vanes 62, as diagrammatically shown in FIG. 2 (where it is again noted that the housing 72 is shown in phantom lines to reveal the view through the orifice 48). The housing or enclosure 72 (or other frame or support) optionally includes mating features and/or a support surface (not shown) for positioning the optical surface profilometry device 70 in a fixed position over the orifice 48 of the cyclonic steam separator 40 with the optical components of the optical surface profilometry device 70 positioned to view inside the orifice 48 with the center of the baseplate 60 approximately centered in the field-of-view of the optical surface profilometry device 70.

The illustrative optical surface profilometry device 70 includes an optical carriage 74 with a linear array of lasers (not shown) forming linear illumination 76 on the surface of the baseplate 60 oriented along one lateral dimension (denoted the "x" direction in FIG. 2). The linear illumination 76 is scanned in the transverse direction (denoted the "y" direction in FIG. 2) to provide two-dimensional area acquisition. In illustrative FIG. 2, the scanning is implemented mechanically by mounting the optical carriage 74 on tracks or rails 78 and moving the optical carriage 74 in the y-direction along the tracks or rails 78 using suitable mechanical gearing 80. In another suitable approach (not shown), the scanning can be implemented optically, e.g. using a tilting mirror or lens or other beam-steering apparatus to scan the linear illumination 76 across the surface of the baseplate 60. It is also contemplated to replace the illustrative linear light source with a point light source (e.g. a single laser beam) that is rastered mechanically or via beam steering optics in both x- and y-directions to achieve two-dimensional scanning. The optical carriage 74 further includes photodiodes or other optical detectors (not shown) that detect the reflected light and estimate depth of the surface of the baseplate 60 (in the "third dimension" transverse to both the x- and y-directions). This estimate can employ various techniques.

In one approach, the linear illumination 76 is tilted or canted at a small cant angle to the surface normal of the baseplate 60, for example, in the y-direction, and surface depth is measured based on the lateral (for example, y-directional) shift of the reflected light. For example, if the light source-to-baseplate 60 surface distance is $z_0+\Delta z$ where $z_0$ is the nominal baseplate surface (for example, without degradation), and $\Delta z$ is the "etch depth" due to surface deviation, and the linear illumination 76 is canted at a small angle $\theta$, then the lateral shift $\Delta x/2$ of the beam traveling from the light source to the surface of the baseplate 60 is $$\tan(\theta) = \frac{\Delta x/2}{z_0 + \Delta z}.$$

Accounting also for the reflection path (from the baseplate surface back to the optical detectors) yields $$2\tan(\theta) = \frac{\Delta x}{z_0 + \Delta z}$$

where $\Delta x$ is the lateral shift observed at the detector. Solving yields surface depth $$\Delta z = \frac{\Delta x}{2\tan(\theta)} - z_0.$$

If the laser beam cant angle $\theta$ is sufficiently small then the small-angle approximation $\tan(\theta) \sim \theta$ can be applied, yielding $$\Delta z = \frac{\Delta x}{2\theta} - z_0$$

so that surface depth $\Delta z$ is proportional to measured linear shift $\Delta x$ with proportionality $1/2\theta$ which is a constant for the optical profilometry system.

In other approaches, the optical surface profilometry system may employ detection of an optical phase shift (for example, using interferometry), a time-of-flight approach using a fast-pulsed laser and high-speed optical detectors, or so forth.

It is to be appreciated that the optical surface profilometry device 70 described with reference to FIGS. 1 and 2 is merely an illustrative example. The optical surface profilometry actually performed on cyclonic steam separator baseplates as described herein employed a Micro-Epsilon brand, model scanCONTROL 2700 device (one of several commercially available profilometry devices) available from Micro-Epsilon USA, Raleigh, N.C., USA in conjunction with a custom-built enclosure and translatable optical carriage corresponding to the illustrative housing 72, optical carriage 74 and mechanics 78, 80 to provide mechanical support and transverse scanning. In optical surface profilometry actually performed on cyclonic steam separator baseplates it was found that surface degradation typically leads to surface variations in the order of hundredths of an inch (that is, in the order of millimeters), which was readily measured with precision of 0.01 inches (0.25 millimeter) or better using the optical surface profilometer.

With reference to FIG. 1, the optical surface profilometry device 70 receives power and control signals from an optical surface profilometer controller 90, which may for example be implemented by suitable programming of a computer 92 or other electronic data processing device. The control software controls the optical carriage 74 to operate its lasers and optical detectors to acquire profilometry data, and to operate the mechanical drive 80 (or optical beam tilting apparatus, if alternatively employed) to perform the scanning. FIG. 1 shows the optical surface profilometer controller 90 connected with the optical surface profilometry device 70 by a physical cable—alternatively, if the profilometry device 70 has on-board power (for example, battery-powered) then a wireless connection between the controller 90 and profilometry device 70 may be employed.

The output of the optical surface profilometry device 70 and profilometer controller 90 for a given baseplate 60 is a set of depth-versus-linear (x) position curves spaced apart along the transverse (y) direction so as to form a two-dimensional map of the baseplate 60. This data acquisition may be repeated for each operational cyclonic steam separator 40 in the steam drum 16. An analysis computer 100 or other electronic data processing device processes the acquired optical surface profilometry data in various ways. In Illustrative FIG. 1, the analysis computer 100 is programmed by suitable software to implement a baseplate mapper module 102 that generates a two-dimensional surface profile map for the baseplate 60 of each cyclonic steam separator 40. This is readily generated as the optical surface profilometer 70, 90 outputs depth-versus-linear (x) position curves spaced apart along the transverse (y) direction, which is a two-dimensional map. The analysis computer 100 is further programmed by suitable software to implement a quantitative analysis module 104 that measures quantitative values such as maximum degradation depth, lateral area (or radius, or diameter) of degradation, or so forth. The analysis computer 100 is further programmed by suitable software to implement a separator head mapper module 106 that classifies the status of each cyclonic steam separator 40 as to whether its baseplate 60 needs maintenance (or, optionally, whether it should be further monitored).

In illustrative FIG. 1, the computer 92 embodying the profilometer controller 90 is separate from the computer 100 embodying the mapping/analysis modules, but alternatively the same computer can be programmed to perform both functions. To store historical data to facilitate comparisons over time, as well as to perform predictive modeling or trending analysis of component condition or degradation, the optical surface profilometry data (raw and/or after processing by the modules 102, 104, 106) are preferably stored in a non-volatile data storage 110, e.g. a hard disk drive, RAID (redundant array of independent disks), or so forth. It is also to be appreciated that the analysis modules 102, 104, 106 and the profilometer control software may be embodied as a non-transitory storage medium storing software executed by the computer(s) 92, 100 to perform the disclosed analysis/control. The non-transitory storage medium may, for example, comprise a hard disk or other magnetic storage medium, an optical disk or other optical storage medium, random access memory (RAM), read-only memory (ROM), flash memory, or other electronic storage medium, various combinations thereof, or so forth.

Although not illustrated, it is contemplated (as described above) to incorporate an integral camera into the optical surface profilometry device 70, so as to perform visual inspection comprising a photographic or digital image record of the state of the baseplate 60. For example, the camera can be mounted on the enclosure or frame or housing 72 oriented to take an image of the baseplate 60 through the orifice 48 of the cyclonic steam separator. In the illustrative example the photograph or digital image can be acquired with the optical carriage 74 moved to an edge location so as to not occlude the camera field-of-view. Other camera arrangements are contemplated. Advantageously this enables acquiring both surface profilometry data and a visual inspection record in automated fashion.

Figure 3:
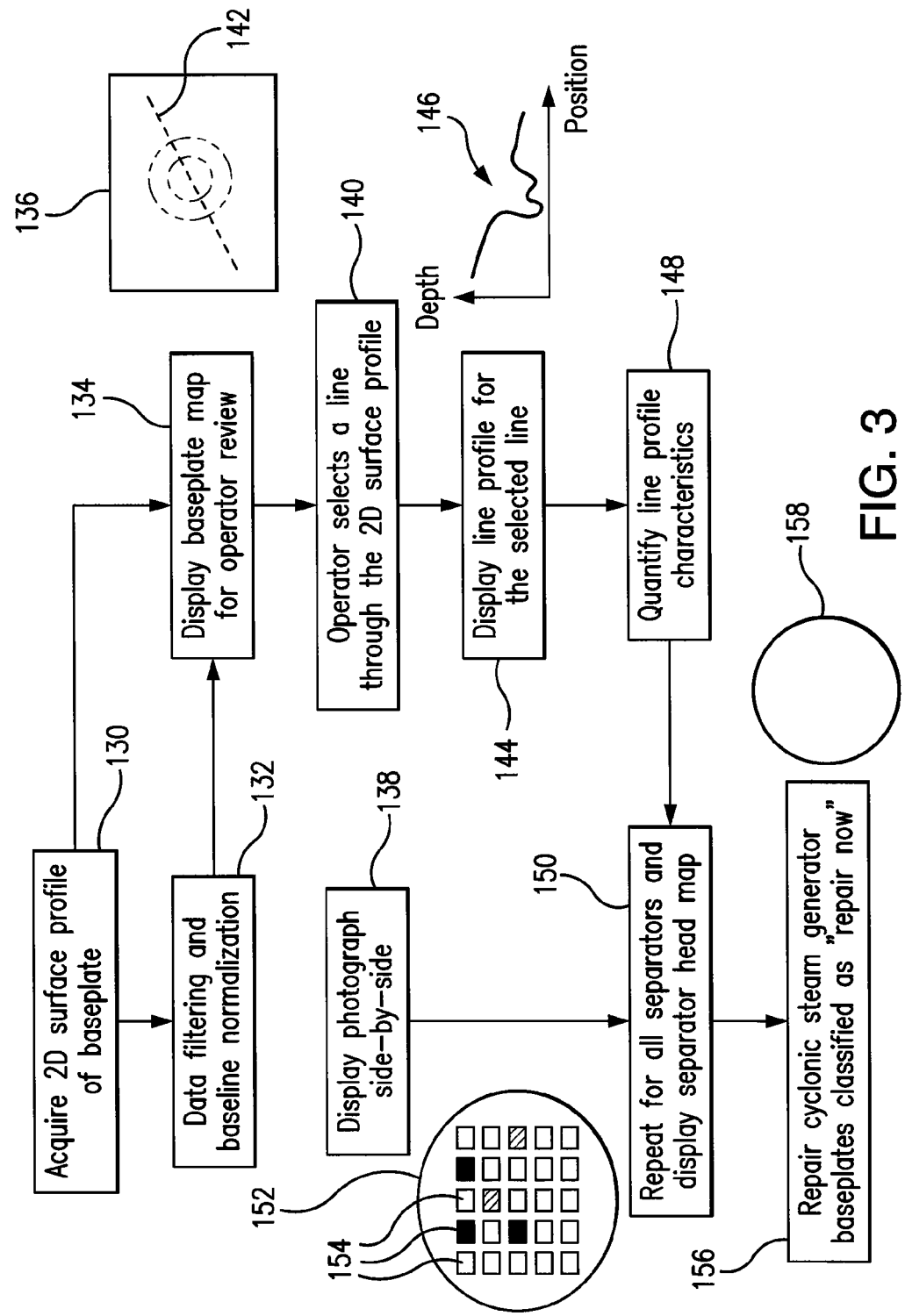
FIG. 3 diagrammatically shows a cyclonic steam separator baseplate inspection process suitably performed using the inspection system of FIG. 1.

With continuing reference to FIGS. 1 and 2 and with further reference to FIG. 3, an illustrative inspection process is described, which is suitably performed during maintenance of the steam generator. (During maintenance, the steam generator is taken offline, depressurized, and its internal components are accessed for inspection and maintenance via manways, vessel head removal, or the like. The various inspection and maintenance operations may be done manually, using robotics, or by a combination of manual and robotic operations). In an operation 130, the optical surface profilometry device 70, 90 along with the mapper module 102 are employed to acquire a surface map of the baseplate 60 of a cyclonic steam separator 40. An optional operation 132 performs optional data filtering and/or baseline normalization. For example, if it is assumed that the outboard regions of the baseplate 60 are substantially not degraded, then these values can be set to the reference depth $z_0$ assumed for a surface with no degradation. A baseline correction, e.g. a linear or quadratic baseline correction, can then be applied between the outboard regions so as to correct for any error due to the baseplate 60 being tilted relative to the profilometry device 70 during the surface profilometry data acquisition. The operation 132 can perform other corrections or filtering, such as removing outliers (for example, unrealistic depth values possibly due to particulates or other defects), performing data smoothing, or so forth.

In an operation 134, the map (for example, a 2D surface profile) of the baseplate 60 is displayed on a display device (for example, a display of the computer 90 or the computer 100) for operator review. For example, the map without correction may be displayed on the computer 90 just after acquisition for immediate or real-time review by the operator, while the map with the corrections 132 may be displayed on the computer 100 for review at a later time. FIG. 3 shows a diagrammatic representation 136 of a typical surface profile map for a baseplate. If the optical surface profilometry device 70 includes a camera, then in an optional operation 138 a photograph or digital image of the baseplate may be displayed side-by-side with the surface profile map 136 for convenient comparison. In an alternate embodiment, the photograph or digital image may be evaluated in conjunction with the profile map as part of the evaluation criteria. In another embodiment, the map may be representative of a portion of the examined area (or entire examined area) rather than a series or collection of individual baseplates.

To perform quantitative analysis, in an operation 140 the operator selects a line 142 through the 2D surface profile 136, for example using a mouse, trackball, trackpad, or other user interfacing device via which the user identifies two points defining the line 142. The user preferably selects the line 142 to run through the degradation region as seen in the 2D surface profile 136. In an alternative approach, the quantitative analysis module 104 can compute the center-of-mass of the depth profile (for example, center of mass is related to $\Sigma_{all\ pixels} v_i r_i$ where $v_i$ is the depth value of the i-th pixel and $r_i$ is the vector position of the i-th pixel in the 2D surface profile map 136) and automatically select a line passing through the center of mass. In an operation 144, a line profile 146 is displayed for the selected line 142, for example plotting depth value as a function of position along the line 142. In an operation 148, one or more line profile characteristics are optionally quantified, such as the maximum-minimum depth differential, the width of the degradation region, or so forth. The quantification can be automated, manual, or semi-automated (for example, the user moves cursors to select the lowest and highest depth values, or the edges of the degradation region, and the computer then computes the difference or width).

The foregoing operations are suitably performed to inspect the baseplate 60 of each cyclonic steam separator 40, and in an operation 150 the separator head mapper module 106 generates a separator head map 152. The separator head map 152 suitably includes an iconic representation 154 of each cyclonic steam separator (for example, a box corresponding to each steam separator arranged in a pattern corresponding to their physical arrangement in the steam drum 16) that may be color coded to indicate baseplate condition. For example, the color coding can employ: green color to indicate a cyclonic steam separator whose baseplate is in good condition; yellow color to indicate a cyclonic steam separator whose baseplate has substantial surface degradation and needs to be monitored but does not need maintenance in this steam generator opening; and red color to indicate a cyclonic steam separator whose baseplate needs maintenance. In an alternate embodiment, the map may be representative of a portion of the area (or entire area) to be evaluated. Maintenance, where needed, can take various forms, such as: replacement of the cyclonic steam separator as a unit, replacement of the baseplate of the cyclonic steam separator, or attachment of an auxiliary plate 158 on top of the degraded baseplate 60. This latter approach can have some detrimental effect on the efficiency of the cyclonic steam separator 40 since the added auxiliary plate 158 may affect the cyclonic rotation of the wet steam; however, it is a low-cost repair that prevents further degradation of the baseplate 60 and thereby prevents the possibility of fragments of the baseplate 60 flaking off and damaging downstream components in the steam generator 10. In one embodiment, the acquired information or data may be used to perform trending analyses or predictive modeling of component degradation.

While the inspection of surfaces of a cyclonic steam separator has been described, the disclosed approach of employing optical surface profilometry to inspect surfaces is expected to find application in the inspection of surfaces of steam system and primary side components of other systems in which the surfaces are subject to degradation. For example, the steam system, primary side, and balance of plant components may comprise other types of heat exchangers, steam separators, steam pipes, manway seating surfaces, primary heads, secondary heads, gasket seating surfaces nuts, bolts, and bolt threads. Flow accelerated corrosion is a known degradation mechanism for power plant components due to the exposure to fast-flowing water or wet steam, although mechanical degradation or other mechanisms are possible. Analogously to baseplates of the cyclonic steam separators described herein, flow accelerated degradation is expected to produce surface profile changes that correlate with chemical or mechanical-chemical damage to the surfaces, making optical surface profilometry an advantageous quantitative inspection approach suitable for classifying each inspected steam generator component or other system components respective to whether those components require maintenance or replacement.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

We claim:

1. A method comprising:
    acquiring a profile of a surface of a component by an optical profilometry system, the surface being one of a plurality of component surfaces;
    acquiring a photographic image of each surface of the plurality of surfaces concurrent with acquiring the profile of each surface of the plurality surfaces;
    classifying a condition of the surface based on the acquired profile and photographic image, and
    displaying a map of each surface of the plurality of surfaces comprising an iconic representation of each surface of the plurality of surfaces in a pattern corresponding to the physical arrangement of the surfaces with the iconic representation color to visually indicate surface degradation.

2. The method of claim 1 wherein the profile comprises a two-dimensional surface profile.

3. The method of claim 1 wherein the optical profilometry system comprises a laser.

4. The method of claim 3 further comprising illuminating a location on the surface with the laser at an angle normal to the surface and determining a depth at the location on the surface based on a lateral shift of the reflected illumination.

5. The method of claim 1 further comprising concurrently displaying the two-dimensional surface profile and the image of the surface.

6. The method of claim 1 further comprising repairing or replacing the component.

7. A non-transitory storage medium storing instructions readable and executable by a computer to perform operations comprising:
controlling an optical surface profilometry system to acquire a surface profile of a plurality of components;
controlling a camera to acquire a photographic image of the plurality of components concurrent with acquiring the surface profile of the plurality of components;
classifying the plurality of components based on the acquired surface profile and acquired photographic image respective to degradation of the plurality of components;
repeating the acquiring and classifying steps for the plurality of components; and
displaying a map of the plurality of components comprising an iconic representation of the plurality of components in a pattern corresponding to a physical arrangement of the plurality of components with each iconic representation color coded to indicate degradation of each of the plurality of components.

8. An inspection system comprising:
an optical surface profilometry system configured to acquire a profile of a surface of a component;
a camera configured to acquire a photographic image of the surface of the component;
a non-transitory storage medium storing instructions readable and executable by an electronic data processing device;
a computer configured to read and execute instructions stored on the non-transitory storage medium to control the optical surface profilometry system to concurrently acquire the profile and the photographic image and to classify a condition of the surface based on the acquired profile and photographic image, and configured to read and execute instructions stored on the non-transitory storage medium to create and display a map of a plurality of surfaces of the component comprising an iconic representation of the plurality of surfaces of the component in a pattern corresponding to a physical arrangement of the plurality of surfaces with each iconic representation color coded to indicate surface degradation.

9. The inspection system of claim 8 wherein the optical surface profilometry system is configured to interface with the component and wherein the computer is configured to read and execute the instructions stored on the non-transitory storage medium to control the optical surface profilometry system to acquire the profile of the surface, to control the camera to acquire the photographic image of the surface, and to classify the condition of the surface based on the acquired profile and photographic image of the surface.

10. The inspection system of claim 8 wherein the optical surface profilometry system comprises a laser profilometry system configured to illuminate a location on a surface with a laser at an angle respective to a surface normal of the surface and computing a surface depth at the location on the surface based on a lateral shift of the reflected illumination.

11. The inspection system of claim 8 wherein the non-transitory storage medium performs operations comprising:
controlling an optical surface profilometry system to acquire the profile of the surface; and
classifying the condition of the surface based on the acquired profile.

12. A method of inspecting a component subject to degradation, the method comprising:
acquiring at a first time a first profile of a surface of the component with an optical surface profilometry system and a first photographic image of the surface;
acquiring at a second time a second profile of the surface of the component and a second photographic image of the surface of the component classifying a first condition of the component based on the acquired first profile and first photographic image;
classifying a second condition of the component based on the acquired second profile and first photographic image component, and creating and displaying a map of a plurality of surfaces of the component comprising an iconic representation of the plurality of surfaces of the component in a pattern corresponding to a physical arrangement of the plurality of surfaces with each iconic representation color coded to indicate surface degradation.

13. The method of claim 12 further comprising:
illuminating a location on the surface of the component with a laser of the optical profilometry system at an angle respective to a surface normal of the surface of the component; and
determining a surface depth at the location on the surface of the component based on a lateral shift of reflected illumination.

14. The method of claim 12 further comprising trending degradation of the component based on data obtained from the compared first and second conditions of the component.

15. The method of claim 12 further comprising developing a predictive model of degradation of the component based on data obtained from the compared first and second conditions of the component.

16. The method of claim 12 wherein a camera is integrated with the optical surface profilometry system.

17. The method of claim 12 wherein the component comprises a baseplate of a cyclonic steam separator.

* * * * *